United States Patent [19]

Oksman et al.

[11] Patent Number: 5,289,132
[45] Date of Patent: Feb. 22, 1994

[54] VOLTAGE CHARACTERISTIC COMPARATOR FOR DISCRIMINATING SOLUTIONS

[76] Inventors: Henry C. Oksman, 20 Wagon Wheel Rd., Mamaroneck, N.Y. 10543; Joseph Eisner, 185 E. 85th St., New York, N.Y. 10028

[21] Appl. No.: 800,910
[22] Filed: Dec. 4, 1991
[51] Int. Cl.⁵ .............................................. G01N 27/06
[52] U.S. Cl. ................................... 324/444; 324/439; 324/713; 204/407; 422/82.02
[58] Field of Search ............... 324/438, 439, 444, 698, 324/713; 204/407; 422/82.02

[56] References Cited

U.S. PATENT DOCUMENTS

| | | | |
|---|---|---|---|
| 3,100,985 | 8/1963 | Wells | 324/439 X |
| 3,293,155 | 12/1966 | Stone | 324/439 X |
| 3,430,129 | 2/1969 | Cardeiro | 324/439 |
| 3,450,984 | 6/1969 | Holmes | 324/439 X |
| 4,728,943 | 3/1988 | Vermeiren | 324/698 X |
| 4,853,638 | 8/1989 | Endou et al. | 324/439 X |
| 5,081,420 | 1/1992 | Fullenwider | 324/438 |
| 5,124,659 | 6/1992 | Frola et al. | 324/438 |

Primary Examiner—Kenneth A. Wieder
Assistant Examiner—Glenn W. Brown
Attorney, Agent, or Firm—Fiddler Levine & Mandelbaum

[57] ABSTRACT

An apparatus and method for rapidly identifying the chemical compositions and concentrations of solutions and for discriminating among solutions of different chemical compositions and concentrations of the solution is monitored by applying across a predetermined volume of the solution a predetermined voltage for a predetermined time after which the application of voltage is terminated and the voltage time characteristic measured across the solution as the voltage decays is compared with an empirically obtained voltage versus time characteristic for a solution having a standardized composition and/or concentration.

6 Claims, 6 Drawing Sheets

VOLTAGE CHARACTERISTIC COMPARATOR FOR DISCRIMINATING SOLUTIONS

BACKGROUND OF THE INVENTION

Many solutions for industrial, medical, or other purposes cannot be readily distinguished by the senses. That is, they may look similar. e.g., colorless or of similar color. and may smell alike, e.g., odorless or having similar odors. For safety and/or hygienic reasons, depending on the nature of the solutions, it may be inconvenient or even dangerous to taste or even touch them.

Various chemical tests are known for identifying or distinguishing among various solutions. These tests generally require that the subject solution be mixed with chemicals or other contaminating substances which render the portion of solution that is tested, thereafter, unusable. Also, chemical tests are generally time consuming, require stocking and restocking of the test chemicals, and necessitate a disposal apparatus for discarding the test solution.

SUMMARY OF THE INVENTION

The present invention overcomes the aforementioned disadvantages of prior art solution discrimination systems in providing for a method and device for identifying and/or discriminating among solutions which is rapid, avoids contamination, and requires no consumable constituents. More specifically the present invention provides for an apparatus for distinguishing a solution including container means for storing the solution, first and second electrode means mounted proximate to the container means for immersion in the solution when stored in the container, switch means having first terminal means connected to one of the electrodes means and second terminal means, a voltage source having first terminal means connected to the switch means' first terminal means and second terminal means connected to the other of the electrodes, timer means connected to the switch means for controlling the duration of application of the voltage source to the electrodes, waveform monitoring means connected to the first and second electrodes for monitoring the amplitude versus time characteristic of the voltage between the electrodes, display means for displaying the amplitude versus time characteristic, sampling means for storing measured signals representative of the amplitude of the amplitude versus time characteristic at predetermined times, reference means for storing standard signals representative of the amplitude of a standard amplitude versus time characteristic at the predetermined times, comparator means operatively connected to the sampling means and the reference means for comparing the standard and reference signals corresponding to the predetermined times and producing a signal indicative of the outcome of the comparison, and indicator means operatively connected and responsive to the comparator means for producing an indication of the outcome of the comparison.

It is, therefore, an object of the invention to provide an apparatus and method for discriminating among solutions without contaminating the solution under test.

Another object of the invention is to provide an apparatus and method for discriminating among solutions that can be done rapidly and inexpensively.

Still another object of the invention is to provide an apparatus and method for discriminating among solutions that can be done without any chemical additives.

A further object of the invention is to provide an apparatus and method for discriminating among solutions that compares the voltage versus time discharge characteristic of the solution under test with that of a standard solution.

Other and further objects of the invention will be apparent from the following drawings and description of a preferred embodiment of the invention in which like reference numerals are used to designate like parts in the various views.

DESCRIPTION OF THE PREFERRED EMBODIMENT OF THE INVENTION

Figure 1:
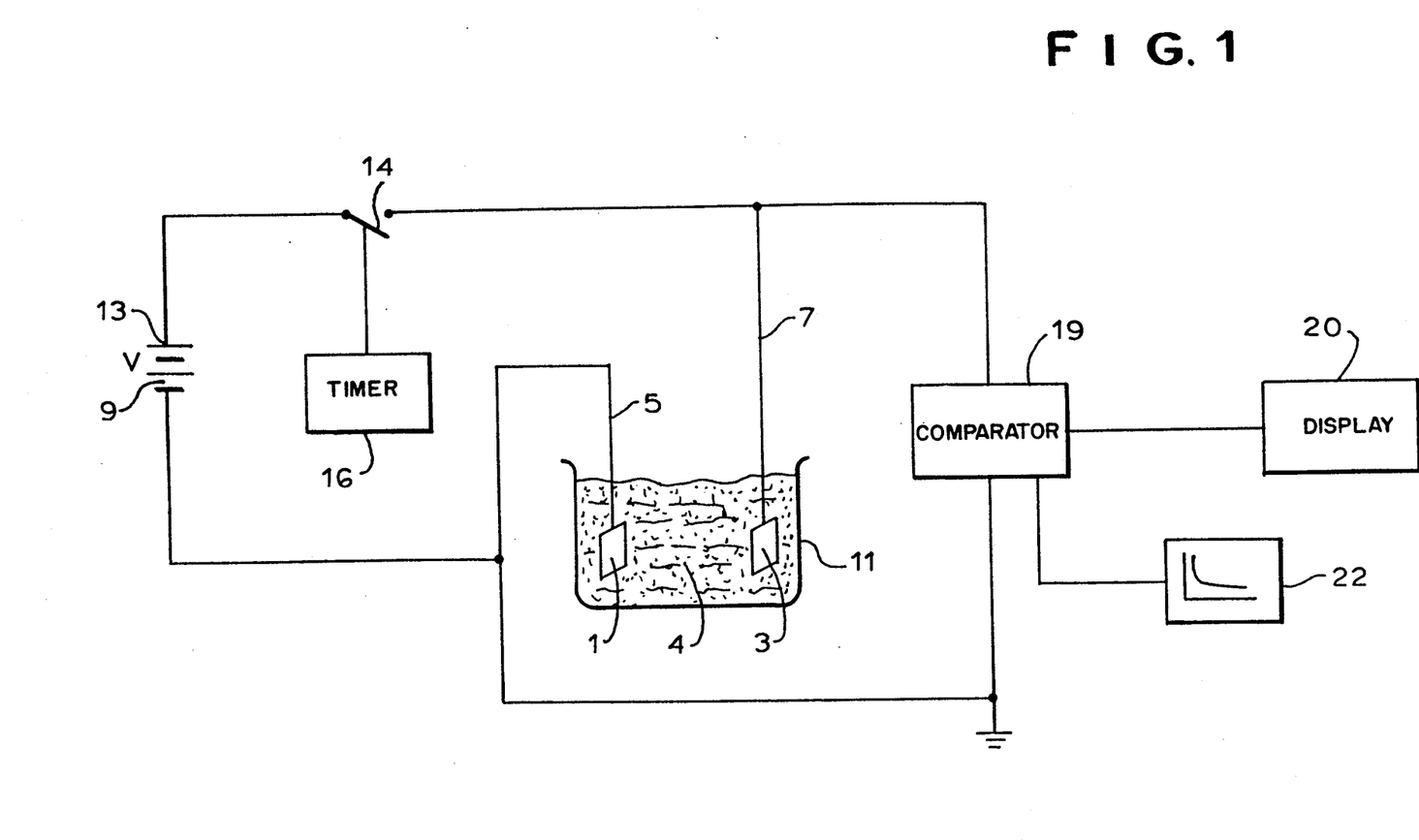
FIG. 1 is a schematic diagram of the apparatus of the preferred embodiment of the invention.

Referring now to FIG. 1 of the drawings, a pair of electrodes 1 and 3 is connected by respective leads 5 and 7 to a source of direct current 9. The electrodes 1 and 3 are disposed within a container 11 filled with a predetermined volume of a solution 4 of unknown quantity or concentration.

Connected in series between the positive terminal 13 of voltage source 9 is a normally open switch 14 controlled by a timer 16. The timer 16 is conventional and can be adjusted to close the switch 14 at a predetermined time for a predetermined duration. In the preferred embodiment of the invention, the predetermined duration of the period during which the switch 14 is closed is two seconds.

Connected to leads 5 and 7 is a voltage versus time waveform comparator 19 for comparing the voltage versus time waveform during the discharge following the reopening of the switch 14 with the voltage versus time waveform of a standard solution stored in a memory device 22. A standard solution is one to which the solution under test is being compared to determine whether the solution under test has its composition and/or concentration. A display 20 can be provided for displaying the voltage across the electrodes 1 and 3 in the solution 4. The device 19 is one capable of comparing voltage waveforms measured over predetermined time intervals and its construction will be known to those skilled in the art.

EXAMPLE 1

Figure 2A:
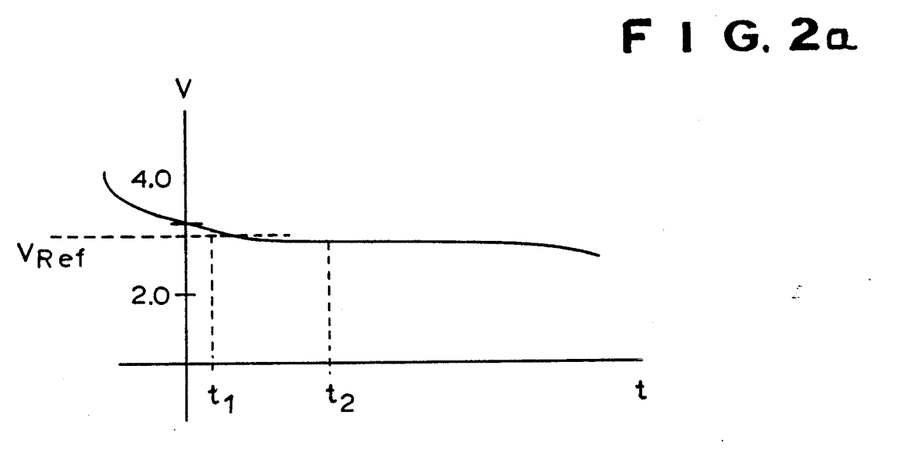
FIG. 2a is a plot of the voltage versus time characteristic obtained by applying the method of the preferred embodiment of the invention to a first solution.

Referring now to FIG. 2a, there is shown the voltage versus time characteristic of the voltage observed across leads 5 and 7 of FIG. 1 for a 0.9% solution of saline immediately following the application of 10 volts D.C. to the electrodes 1 and 3 by closing the switch 14 for two seconds and thereafter reopening it. As can be seen in FIG. 2a, the voltage immediately drops to about 4 volts and remains constant for about 40 seconds after which the voltage decays very slowly.

Figure 2B:
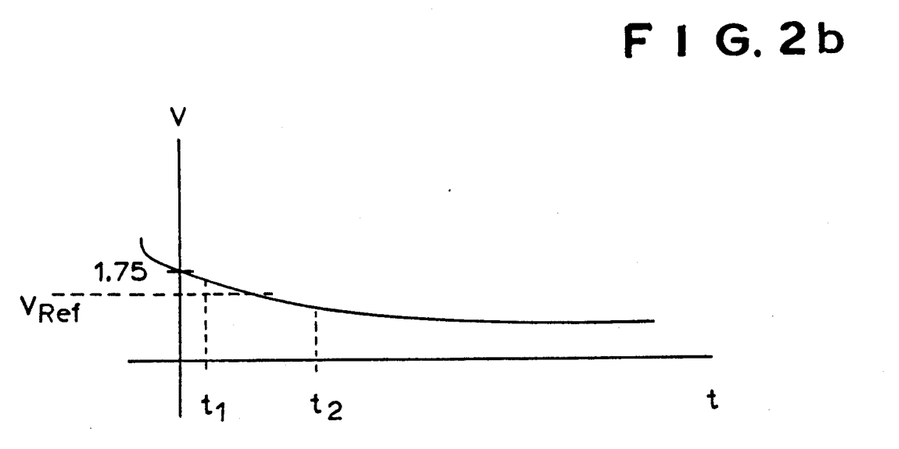
FIG. 2b is a plot of the voltage versus time characteristic obtained by applying the method of the preferred embodiment of the invention to a second solution.

Referring now to FIG. 2b, there is shown the voltage versus time characteristic of the voltage observed across leads 5 and 7 of FIG. 1 for a solution of saline containing 1 part of a 3% hydrogen peroxide solution for each 6 parts of the saline, again, immediately following the application of 10 volts D.C. to the electrodes 1 and 3 by closing the switch 14 for 2 seconds and thereafter reopening it. As can be seen in FIG. 2b, the voltage immediately drops to about 1.75 volts and decays to a steady state voltage of about 1.1 volts within 5 seconds. Further testing has shown that as the concentration of the hydrogen peroxide is increased relative to the saline, the magnitude of the initial voltage drop increases and the steady state voltage level decreases.

The data observed for various concentrations of saline and hydrogen peroxide solution under the above conditions are shown in Table 1.

TABLE 1

| Applied voltage = | 10 volts |
| Electrode area = | 150 mm$^2$ (6 mm × 25 mm) |
| Spacing between electrodes = | 60 mm |
| Volume of solution = | 7 cc |

| Parts Saline | Parts hydrogen peroxide | Volts 0 sec | Volts 1 sec | Volts 5 sec |
| --- | --- | --- | --- | --- |
| 7 | 0 | 4.1 | 4.0 | 4.0 |
| 6 | 1 | 1.75 | 1.65 | 1.1 |
| 5 | 2 | 1.7 | 1.6 | 1.0 |
| 4 | 3 | 1.6 | 1.2 | 0.6 |
| 3 | 4 | 0.8 | 0.5 | 0.2 |
| 2 | 5 | 0.3 | 0.2 | 0.1 |
| 1 | 6 | 0.15 | 0.1 | 0.05 |
| 0 | 7 | 0.1 | 0.075 | 0.01 |

Figure 3A:
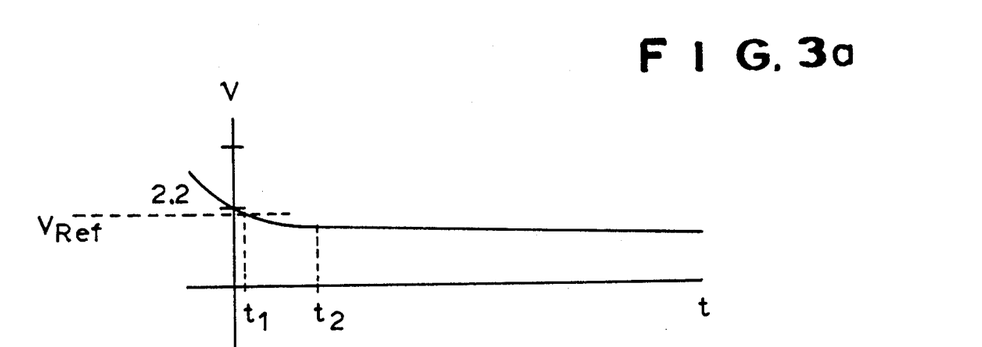
FIG. 3a is a plot of the voltage versus time characteristic obtained by applying the method of the preferred embodiment of the invention to a third solution.

Similar tests were done using a solution of sodium sulfate, Na$_2$SO$_4$ instead of saline. Referring now to FIG. 3a, there is shown the voltage versus time characteristic of the voltage observed across leads 5 and 7 of FIG. 1 for a 2.2_% solution of sodium sulfate immediately following the application of 10 volts D.C. to the electrodes 1 and 3 by closing the switch 14 for two seconds and, thereafter, reopening it. As can be seen in FIG. 3a, the voltage immediately drops to about 2.2 volts and thereafter decays very slowly.

Figure 3B:
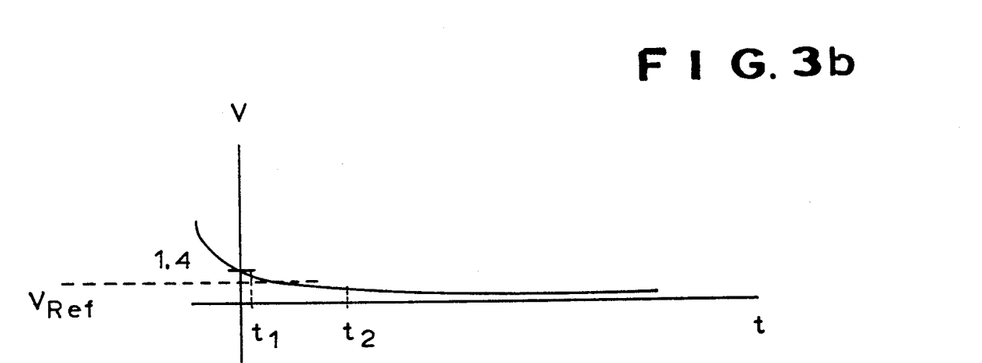
FIG. 3b is a plot of the voltage versus time characteristic obtained by applying the method of the preferred embodiment of the invention to a fourth solution.

Referring now to FIG. 3b, there is shown the voltage versus time characteristic of the voltage observed across leads and 7 of FIG. 1 for a solution of sodium sulfate containing 1 part of a 3% hydrogen peroxide solution for each 6 parts of the sodium sulfate, again, immediately following the application of 10 volts D.C. to the electrodes 1 and 3 by closing the switch 14 for two seconds and thereafter reopening it. As can be seen in FIG. 3b, the voltage immediately drops to about 1.4 volts and continues to decay, but more slowly. Further testing has shown that as the concentration of the hydrogen peroxide is increased relative to the sodium sulfate, the magnitude of the initial voltage drop increases as does the rate of decay thereafter.

The data observed for various concentrations of sodium sulfate and hydrogen peroxide are shown in Table 2.

TABLE 2

| Applied voltage = | 10 volts |
| Electrode area = | 150 mm$^2$ (6 mm × 25 mm) |
| Spacing between electrodes = | 60 mm |
| Volume of solution = | 7 cc |

| Parts NA$_2$SO$_4$ | Parts hydrogen peroxide | Volts 0 sec | Volts 1 sec | Volts 3 sec |
| --- | --- | --- | --- | --- |
| 7 | 0 | 2.2 | 2.0 | 1.95 |
| 6 | 1 | 1.4 | 0.9 | 0.7 |
| 5 | 2 | 1.3 | 0.8 | 0.4 |
| 4 | 3 | 1.2 | 0.7 | 0.3 |
| 3 | 4 | 1.1 | 0.6 | 0.3 |
| 2 | 5 | 1.0 | 0.5 | 0.2 |
| 1 | 6 | 0.9 | 0.4 | 0.1 |
| 0 | 7 | 0.8 | 0.3 | 0.0 |

The solution under test in the container 11 is preferably one to which a known quantity of a conductive salt has been added. The use of a salt in the solution serves two purposes. First it renders the solution conductive so that it can pass current in circuit with the voltage source. Secondly, the introduction of the salt into the solution makes the solution electrolytic. The combination of the electrolyte and terminals selected from among the appropriate metals, e.g. rhodium, nickel, paladium, platinum, carbon and similar heavy group metals which poorly oxidize, _acts as a battery to initially maintain a voltage difference across the electrodes when the switch 14 is opened and the voltage source is disconnected from the electrode 1. A dielectric effect is also believed to contribute to the sustenance of the voltage between the electrodes and the different voltage versus time characteristics for solutions of different compositions and concentrations.

Depending on the composition of the non-salt component of the solution, it can conduct in a way that causes the residual voltage across the electrodes 1 and 3 to decay much more rapidly then it would where the only solvent in the solution is the salt. Tests with hydrogen peroxide show that after the voltage source 9 is disconnected from the electrode 1 by the timer 16 and switch 14, there is sometimes a brief period during which the voltage across the electrodes is held almost at its original level with very slow decay followed by a sudden drop believed attributable to electrochemical effects on the dissolved constituents of the solution, including ionization and the generation of active free radicals of the elements of the compounds dissolved in the solution.

Figure 4:
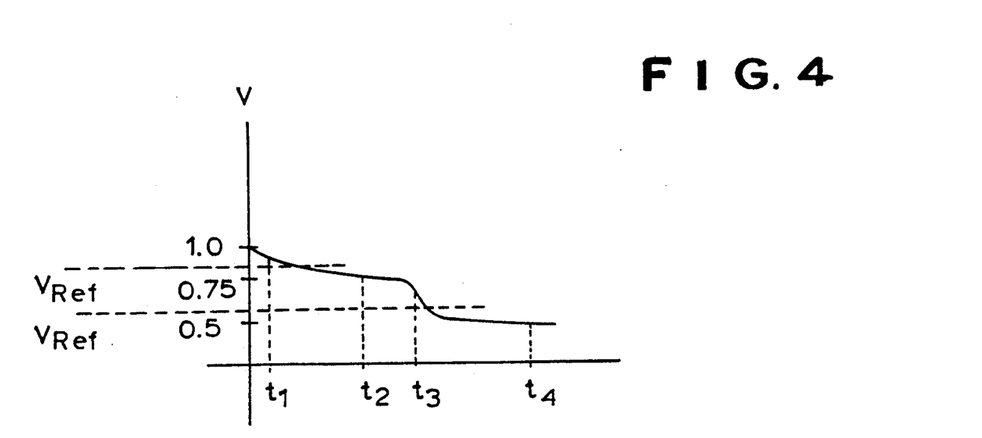
FIG. 4 is a plot of the voltage versus time characteristic obtained by applying the method of the preferred embodiment of the invention to a fifth solution.

Referring now to FIG. 4, there is shown the voltage versus time discharge characteristic for a solution containing more than one salt mixed with hydrogen peroxide. Specifically the solution is made up of 0.8% NaCl, 2.0% NaSO$_4$, and 0.5% H$_2$O$_2$ As can be seen from FIG. 4, after reopening of the switch 14, the voltage drops to 1 volt from which it decays very slowly for about 1.5 seconds after which the voltage decrease accelerates down to 0.5 volts in about 0.25 seconds. From that point on voltage decay is very slow.

Salts other than sodium chloride (saline) and sodium sulfate may be used. The halides of sodium and potassium are generally suitable for use with the discrimination method and apparatus herein disclosed.

Figure 5:
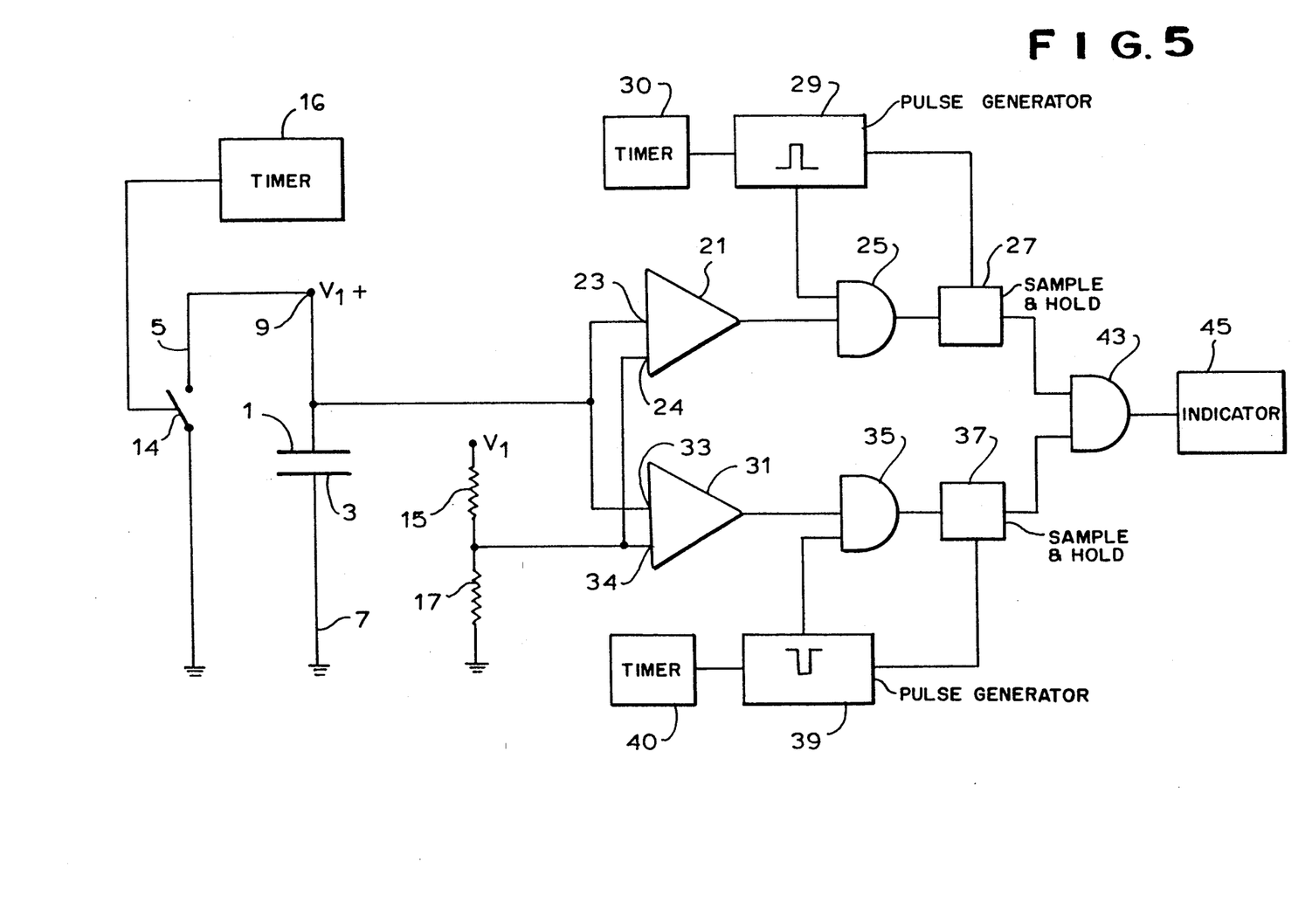
FIG. 5 is a schematic diagram of the apparatus of another preferred embodiment of the invention.

Referring now to FIG. 5 of the drawings, an apparatus for identifying a solution having a voltage versus time discharge characteristic of the form shown in FIGS. 2a,b and 3a,b will be described. A pair of electrodes 1 and 3, as in FIG. 1, is connected by respective leads 5 and 7 to a source of direct current 9. The electrodes 1 and 3 are disposed within a container (see FIG. 1) filled with a predetermined volume of the solution of unknown quantity or concentration.

Connected in series between the positive terminal 13 of voltage source 9, as in FIG. 1, is a normally open switch 14 controlled by a timer 16 which can be adjusted to close the switch 14 at a predetermined time for a predetermined duration, e.g. two seconds.

A comparator 21 has an input terminal 23 connected to the electrode 1. The other input terminal 24 of the comparator 21 is connected between two series resistors 15 and 17 arranged in a voltage divider configuration with resistor 15 connected to a constant power supply voltage $V_1$ and resistor 17 connected to circuit ground. The values of the resistors 15 and 17 are chosen so that the voltage between them is equal to a reference voltage $V_{REF}$ (see FIGS. 2a, 2b, 3a, 3b). The reference voltage $V_{REF}$ is selected to be about midway between the high and low voltages across electrodes 1 and 3 measured for a standard solution to which the specimen solution under test is being compared, over a time interval $t_1-t_2$, after reopening of the switch 14.

The output of the comparator 21 is connected to one input of an AND gate 25, the other input of which is connected to a pulse generator circuit 29 controlled by a timer 30. Pulse generator circuit 29 normally puts out a signal at a low logic level. In response to the timer 30, pulse generator circuit 29 generates a high level pulse at a first predetermined time, $t_1$, after the switch 14 is reopened. The output of the gate 25 at the first predetermined time $t_1$ is stored in a sample and hold circuit 27.

A comparator 31 has an input terminal 33 connected to the electrode 1. The other input terminal 34 of the comparator 31 is connected between the two series resistors 15 and 17.

The output of the comparator 31 is connected to one input of an AND gate 35 The other input of which is connected to a pulse generator circuit 39 controlled by a timer 40. Pulse generator circuit 39 normally generates a signal at a high logic level. In response to the timer 40, pulse generator circuit 39 generates a low level pulse at a second predetermined time, $t_2$, after $t_1$. The output of the gate 35 is stored in a sample and hold circuit 37.

Sample and hold circuits 27 and 37 are connected to an AND gate 43 having an output connected to an indicator 45 which can be an LED display, an audible beeper, or any other signalling device. When a high logic level signal is generated at the output of AND gate 43, indicator 45 provides an indication that the voltage across the solution under test, i.e., enveloping the electrodes 1 and 3, is greater than $V_1$ at the first predetermined time, $t_1$, and less than $V_1$ at the second predetermined time, $t_2$. The presence or absence of the indication signals that the solution under test is or is not of the same composition and concentration as the standard solution to which it is being compared.

The circuit of FIG. 5 is suitable for identifying a solution having a voltage versus time discharge characteristic with a single rapid decrease followed by a slow decay as in FIGS. 2a,b and 3,b. In the case where there are two voltage decelerations as in FIG. 4, or even more, the circuit of FIG. 5 can be extended to test for voltage values $V_{REF}$ and $V_{REF}'$ which are transcended during each deceleration. That is, two voltage levels can be sampled during each deceleration and, respectively, compared with corresponding reference voltages $V_{REF}$ and $R_{REF}'$ which are, respectively, transcended in the time intervals $t_1-t_2$ and $t_3-t_4$ (FIG. 4) when the method is applied to the standard solution. The logic circuitry of FIG. 5 can be extended to give a positive indication only when the voltages measured at times $t_1$ and $t_2$ respectively exceed and are less than the reference voltage $V_{REF}$ and when the voltages measured at times $t_3$ and $t_4$ respectively exceed and are less than the reference voltage $V_{REF}'$.

Figure 6:
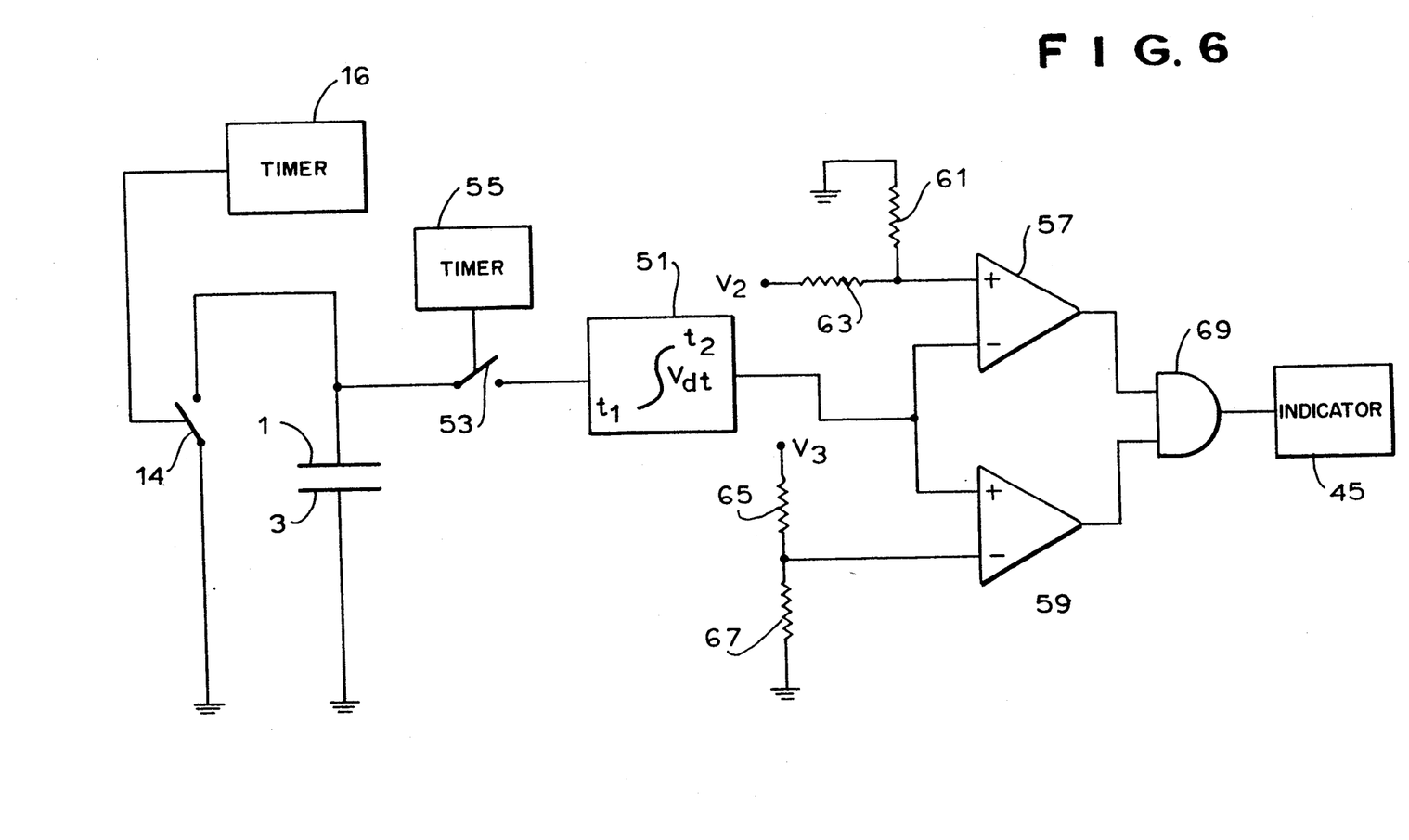
FIG. 6 is a schematic diagram of the apparatus of the still another preferred embodiment of the invention.

In FIG. 6 there is shown, another circuit suitable for comparing the voltage versus time characteristic measured between the electrodes 1 and 3 across the solution under test. The electrodes 1 and 3 are connected to the switch 14 which is, in turn, controlled by a timer 16 as described with respect to FIGS. 1 and 5.

Electrode 1 is connected to the input of an integrator 51 through a switch 53 controlled by a timer 55. The timer 55 closes the switch 53 for a predetermined time interval $t_1-t_2$ after the reopening of the switch 16. The voltage across the electrodes 1 and 3 is integrated over the time interval during which the timer 55 is active to close switch 53.

A voltage proportional to the integral of the voltage across the electrodes 1 and 3 is applied by integrator 51 to inputs of comparators 57 and 59. The other inputs of comparators 57 and 59 are, respectively, connected to a voltage divider network made up of resistors 61 and 63 connected to a voltage supply $V_2$ and to a voltage divider network made up of resistors 65 and 67 connected to a voltage supply $V_3$.

The values of $V_2$ and of resistors 61 and 63 are chosen so that the voltage applied to the positive input of comparator 57 is slightly greater than the integral of the voltage versus time characteristic for the standard solution to which the solution under test is being compared over the time period during which the timer 55 is actuated to close the switch 53. Similarly, the values of $V_3$ and of resistors 65 and 67 are chosen so that the voltage applied to the negative input of comparator 59 is slightly less than the integral of the voltage versus time characteristic for a standard solution to which the solution under test is being compared over the time period during which the timer 55 is actuated to close the switch 53.

The outputs of the comparators 57 and 59 are applied to an AND gate 69, the output of which is connected to an indicating device 45 for providing an indication of whether the solution under test is the same in composition and/or concentration as the standard solution, as explained with respect to FIG. 5.

Figure 7:
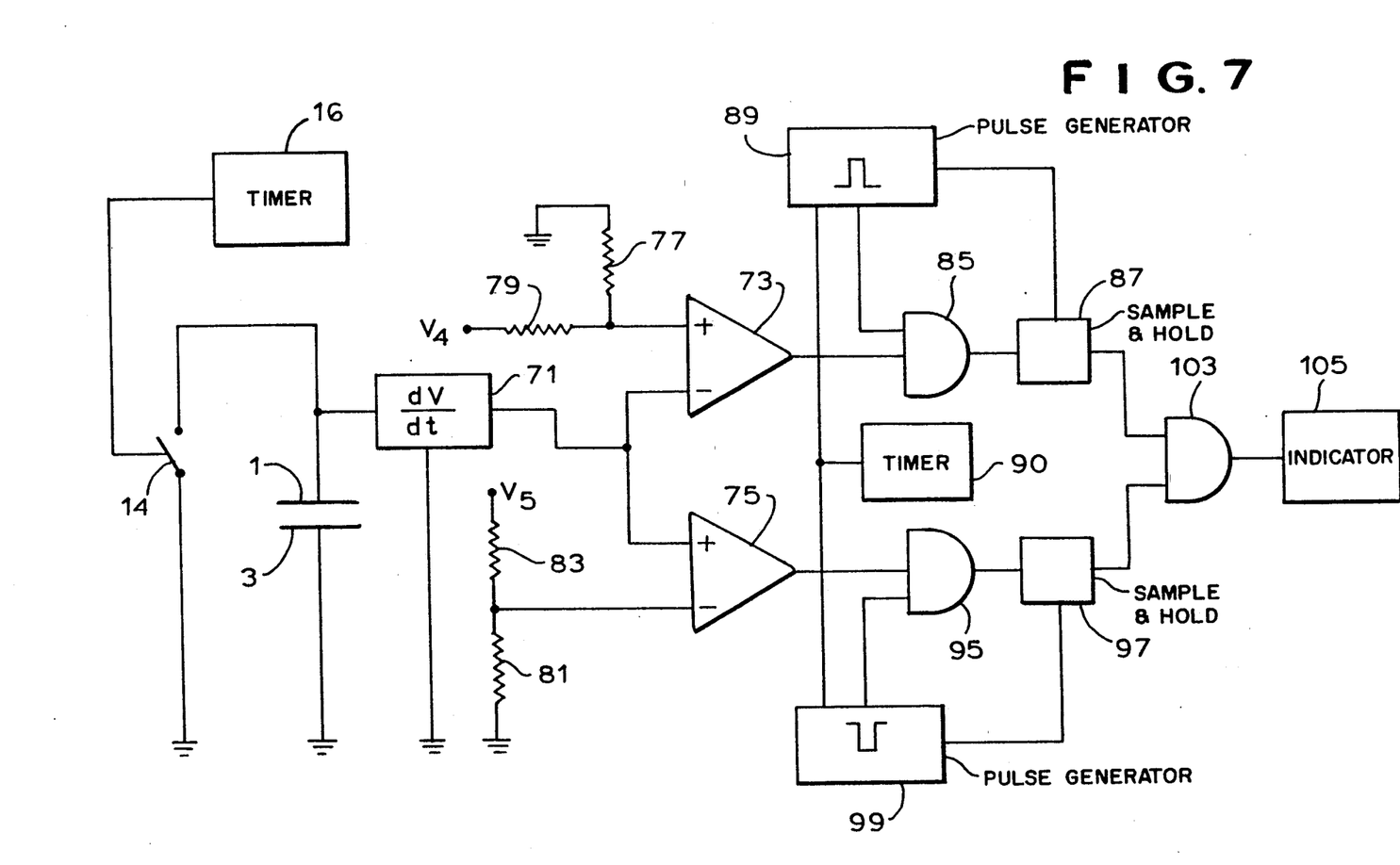
FIG. 7 is a schematic diagram of the apparatus of a further preferred embodiment of the invention.

In FIG. 7 there is shown, another circuit suitable for comparing the voltage versus time characteristic measured between the electrodes 1 and 3 across the solution under test. The electrodes 1 and 3 are connected to the switch 14 which is, in turn, controlled by a timer 16 as described with respect to FIGS. 1, 5 and 6.

Electrode 1 is connected to the input of a differentiator 71 the output of which is connected to comparators 73 and 75. The other inputs of comparators 73 and 75 are, respectively, connected to a voltage divider network made up of resistors 77 and 79 connected to a voltage supply $V_4$ and to a voltage divider network made up of resistors 81 and 83 connected to a voltage supply $V_5$.

The values of $V_4$ and of resistors 77 and 79 are chosen so that the voltage applied to the positive input of comparator 73 is slightly greater than the derivative of the voltage versus time characteristic for a standard solution to which the solution under test is being compared at a predetermined time after the switch 14 is reopened. Similarly, the values of $V_5$ and of resistors 83 and 81 are chosen so that the voltage applied to the negative input of comparator 75 is slightly less than the derivative of the voltage versus time characteristic for a standard solution to which the solution under test is being compared at the same predetermined time.

The output of the comparator 73 is connected to one input of an AND gate 85, the other input of which is connected to a pulse generator circuit 89 controlled by a timer 90. Pulse generator circuit 89 normally puts out a signal at a low logic level. In response to the timer 90, pulse generator circuit 89 generates a high level pulse at the predetermined time, e.g., 0.5 seconds after the switch 14 is reopened. The output of the gate 85 at the first predetermined time $t_1$ is stored in a sample and hold circuit 87.

The output of the comparator 75 is connected to one input of an AND gate 95, the other input of which is connected to a pulse generator circuit 99 controlled by the timer 90. Pulse generator circuit 99 normally puts out a signal at a high logic level. In response to the timer 90, pulse generator circuit 99 generates a low level pulse at the predetermined time. The output of the gate 95 at the predetermined time is stored in a sample and hold circuit 97.

Sample and hold circuits 87 and 97 are connected to an AND gate 103 having an output connected to an indicator 105 which provides an indication, when a high logic level signal is generated at the output of AND gate 103, that the voltage across the solution under test, i.e., enveloping the electrodes 1 and 3, is greater than $V_4$ and less than $V_5$ at the predetermined time, i.e., when timer 90 actuates pulse generators 89 and 99. Such an indication can be interpreted to mean that the composition and/or concentration of the solution under test is the same as the standard solution.

It is to be appreciated that the foregoing is a description of a preferred embodiment of the invention to which variations and modifications may be made without departing from the spirit and scope of the invention. For example, various other curve fitting and comparison techniques, known to those skilled in the art, or combinations thereof, may be used for comparing the voltage versus time characteristics of the discharge voltages across the electrodes 1 and 3. Analog or digital differentiators, integrators, computers, and direct or alternating voltage measuring circuits may be used. Although the examples of the apparatus described above use a D.C. power source, the electrodes 1 and 3 may be energized by an A.C. source. In the latter case, the waveforms will appear differently from when a D.C. source is used to distinguish a solution of like composition and concentration, e.g., due to differing effects on electrons in the constituents of the solution. However, for like A.C. power sources, the waveforms measured across the electrodes will differ according to solution composition and/or concentration.

What is claimed is:

1. Apparatus for distinguishing a solution comprising container means for storing said solution;
    first and second electrode means mounted proximate to said container mean for immersion in said solution when stored in said container,
    switch means having first contact means connected to one of sad electrodes and second contact means;
    a voltage source having first terminal means connected to said switch means' second contact means and second terminal means connected to the other of said electrodes;
    timer means connected to said switch means for actuating sad switch means for applying the voltage of said source to said electrodes for a first period of time and thereafter deactivating said switch means for interrupting application of said voltage to said electrodes; and
    voltage measuring means connected to sad first and second electrodes for measuring the voltage between said electrodes over a second period of time after said switch means is deactivated.

2. Apparatus for distinguishing a solution according to claim 1 wherein said voltage measuring means comprises waveform monitoring means for monitoring the amplitude versus time characteristic of the voltage between said electrodes.

3. Apparatus for distinguishing a solution according to claim 2 wherein said waveform monitoring means comprises integrator means for integrating said waveform over said second period of time.

4. Apparatus for distinguishing a solution according to claim 2 further comprising display means for displaying said amplitude versus time characteristic.

5. Apparatus for distinguishing a solution according to claim 1 further comprising storage means for storing measured signals representative of said voltage during said second period of time;
    reference means for storing standard signals representative of the amplitude of a standard amplitude versus time characteristic; and
    comparator means operatively connected to said storage means and said reference means for comparing said measured and reference signals corresponding to voltages during said second period of time and producing a signal indicative of the outcome of said comparison.

6. Apparatus for distinguishing a solution according to claim 5 further comprising indicator means operatively connected and responsive to said comparator means for producing an indication of the outcome of said comparison.

* * * * *